US007208315B2

(12) United States Patent
Miller et al.

(10) Patent No.: US 7,208,315 B2
(45) Date of Patent: Apr. 24, 2007

(54) COMPOSITIONS AND METHODS FOR EFFICIENT AAV VECTOR PRODUCTION

(75) Inventors: Arthur Dusty Miller, Seattle, WA (US); James M. Allen, Seattle, WA (US); Christine L. Halbert, Bothell, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 53 days.

(21) Appl. No.: 10/169,785

(22) PCT Filed: Jan. 5, 2001

(86) PCT No.: PCT/US01/00429

§ 371 (c)(1),
(2), (4) Date: Nov. 4, 2002

(87) PCT Pub. No.: WO01/49829

PCT Pub. Date: Jul. 12, 2001

(65) Prior Publication Data
US 2004/0248288 A1 Dec. 9, 2004

Related U.S. Application Data

(60) Provisional application No. 60/205,519, filed on May 19, 2000, provisional application No. 60/174,985, filed on Jan. 5, 2000.

(51) Int. Cl.
C12N 15/00 (2006.01)
(52) U.S. Cl. .................. 435/325; 435/320.1; 424/233.1
(58) Field of Classification Search .............. 435/320.1, 435/325; 536/23.1, 24.1; 424/233.1
See application file for complete search history.

(56) References Cited

U.S. PATENT DOCUMENTS 6,004,797 A * 12/1999 Colosi ..................... 435/235.1

FOREIGN PATENT DOCUMENTS

WO 98/27204 6/1998
WO 95/20671 8/1998

OTHER PUBLICATIONS

Xiao et al. Gene Therapy Vectors Based on Adeno-Associated Virus Type 1, Journal of Virology, May 1999, 73(5):3994-4003.*
Verma et al. Gene Therapy-promises, problems and prospects, Nature, 1997, 389:239-242.*
Orkin et al. Report and Recommendations of the Panel to Assess the NIH Investment in Research on Gene Therapy, Dec. 1995, 39 pages, available from http://www.nih.gov/news/panelrep.html.*
Rose, "Parvovirus Reproduction," *Comprehensive Virology*, 3:1-61 (1974).

Graham et al., "Characteristics of a Human Cell Line Transformed by DNA from Human Adenovirus Type 5," *Virology*, 36:59-74 (1977).
Jay et al., "Eukaryotic translational control:Adeno-associated virus protein synthesis is affected by a mutation in the adenovirus DNA-binding protein," *Proc. Natl. Acad. Sci. USA*, 78:2927-2937 (1981).
Richardson and Westphal, "Requirement for Either Early Region 1a or Early Region 1b Adenovirus Gene Products in the Helper Effect for Adeno-Associated Virus," *Journal of Virology*, 51:404-410 (1984).
Laughlin et al., "Latent Infection of KB Cells with Adeno-Associated Virus Type 2," *Journal of Virology*, 60:515-524 (1986).
Tratschin et al., "Negative and Positive Regulation in *trans* of Gene Expression from Adeno-Associated Virus Vectors in Mammalian Cells by a Viral rep Gene Product," *Molecular and Cellular Biology*, 6:2884-2894 (1986).
Samulski et al., "A Recombinant Plasmid from Which an Infectious Adeno-Associated Virus Genome Can Be Excised In Vitro and Its Use To Study Viral Replication," *Journal of Virology*, 61:3096-3101 (1987).
West et al., "Gene Expression in Adeno-Associated Virus Vectors: The Effects of Chimeric mRNA Structure, Helper Virus, and Adenovirus VA, RNA," *Virology*, 160:38-47 (1987).
Beaton et al., "Expression from the Adeno-Associated Virus p5 and p19 Promoters Is Negatively Regulated in *trans* by the *rep* Protein," *Journal of Virology*, 63:4450-4454 (1989).
Chang et al., "Adeno-Associated Virus P5 Promoter Contains an Adenovirus E1A-Inducible Element and a Binding Site for the Major Late Transcription Factor," *Journal of Virology*, 63:3479-3488 (1989).
Samulski et al., "Helper-Free Stocks of Recombinant Adeno-Associated Viruses: Normal Integration Does Not Require Viral Gene Expression," *Journal of Virology*, 63:3822-3828 (1989).
Sandler and Ketner,"Adenovirus Early Region 4 Is Essential for Normal Stability of Late Nuclear RNAs," *Journal of Virology*, 63:624-630 (1989).
Chang and Shenk, "The Adenovirus DNA-Binding Protein Stimulate the Rate of Transcription Directed by Adenovirus and Adeno-Associated Virus Promoters," *Journal of Virology*, 64:2103-2109 (1990).
McCarty et al., "Sequences Required for Coordinate Induction of Adeno-Associated Virus p19 and p40 Promoters by Rep Protein," *Journal of Virology*, 65:2936-2945 (1990).
Shi et al., "Transcriptional Repression by YY1, a Human GLI-Krüppel-Related Protein, and Relief of Repression by Adenovirus E1A Protein," *Cell*, 67:377-388 (1991).

(Continued)

*Primary Examiner*—Stacy B. Chen
(74) *Attorney, Agent, or Firm*—Townsend and Townsend and Crew LLP (57) ABSTRACT

The present invention provides packaging cell lines for the efficient production of an Adeno-associated virus (AAV) vector which does not require "helper" virus function for the replication and encapsidation of the AAV vector particles. Packaging cells, methods for their production and methods for producing recombinant AAV vector particles useful for human gene therapy are provided.

36 Claims, 3 Drawing Sheets

OTHER PUBLICATIONS

Muzyczka, "Use of Adeno-Associated Virus as a General Transduction Vector for Mammalian Cells," *Current Topics in Microbiology and Immunology*, 158:97-129 (1992).

Flotte et al., "Stable *in vivo* expression of the cystic fibrosis transmembrane conductance regulator with an adeno-associated virus vector," *Proc. Natl. Acad. Sci. USA*, 90:10613-10617 (1993).

Nordqvist et al., "Human Adenovirus Encodes Two Proteins Which Have Opposite Effects on Accumulation of Alternatively Spliced mRNAs," *Molecular and Cellular Biology*, 14:437-445 (1994).

Clark et al., "Cell Lines for the Production of Recombinant Adeno-Associated Virus," *Human Gene Therapy*, 6:1329-1341 (1995).

Halbert et al., "Adeno-Associated Virus Vectors Transduce Primary Cells Much Less Efficiently than Immortalized Cells," *Journal of Virology*, 69:1473-1479 (1995).

Hörer et al., "Mutational Analysis of Adeno-Associated Virus Rep Protein-Mediated Inhibition of Heterologous and Homologous Promoters," *Journal of Virology*, 69:5485-5496 (1995).

Kyöstiö et al., "Negative Regulation of the Adeno-Associated Virus (AAV) $P_5$ Promoter Involves both the $P_5$ Rep Binding Site and the Consensus ATP-Binding Motif of the AAV Rep68 Protein," *Journal of Virology*, 69:6787-6796 (1995).

Lewis et al., "Adenovirus EIA Proteins Interact with the Cellular YY1 Transcription Factor," *Journal of Virology*, 69:1628-1636 (1995).

Scaria et al., "Complementation of a human adenovirus early region 4 deletion mutant in 293 cells using adenovirus-polylysine-DNA complexes," *Gene Therapy*, 2:295-298 (1995).

Zaitlin et al., "Alveolar stem cell transduction by an adeno-associated viral vector," *Gene Therapy*, 2:623-631 (1995).

Ferrari et al., "Second-Strand Synthesis Is a Rate-Limiting Step for Efficient Transduction by Recombinant Adeno-Associated Virus Vectors," *Journal of Virology*, 70:3227-3234 (1996).

Kessler et al., "Gene delivery to skeletal muscle results in sustained expression and systemic delivery of a therapeutic protein," *Proc. Natl. Acad. Sci. USA*, 93:14082-14087 (1996).

Allen et al., "Identification and Elimination of Replication-Competent Adeno-Associated Virus (AAV) That Can Aris by Nonhomologous Recombination during AAV Vector Production," *Journal of Virology*, 71:6816-6822 (1997).

Clark et al., "Recombinant Adeno-Associated Viral Vectors Mediate Long-Term Transgene Expression in Muscle," *Human Gene Therapy*, 8:659-669 (1997).

Fisher et al., "Recombinant adeno-associated virus for muscle directed gene therapy," *Nature Medicine*, 3:306-312 (1997).

Herzog et al., "Stable gene transfer and expression of human blood coagulation factor IX after intramuscular injection of recombinant adeno-associated virus," *Proc. Natl. Acad. Sci. USA*, 94:5804-5809 (1997).

Koeberl et al., "Persistent expression of human clotting factor IX from mouse liver after intravenous injection of adeno-associated virus vectors," *Proc. Natl. Acad. Sci. USA*, 94:1426-1431 (1997).

Leppard, "E4 gene function in adenovirus, adenovirus vector and adeno-associated virus infections," *Journal of General Virology*, 78:2131-2138 (1997).

Li et al., "Role for Highly Regulated *rep* Gene Expression in Adeno-Associated Virus Vector Production," *Journal of Virology*, 71:5236-5243 (1997).

Synder et al., "Persistent and therapeutic concentrations of human factor IX in mice after hepatic gene transfer of recombinant AAV vectors," *Nature Genetics*, 16:270-276 (1997).

Weger et al., "Control of Adeno-Associated Virus Type 2 Cap Gene Expression: Relative Influence of Helper Virus, Terminal Repeats, and Rep Proteins," *Journal of Virology*, 71:8437-8447 (1997).

Xiao et al., "Adeno-associated virus (AAV) vector antisense gene transfer in vivo decreases $GABA_A$ $\alpha_1$ containing receptors and increases inferior collicular seizsure sensitivity," *Brain Research*, 756:76-83 (1997).

Gao et al., "High-Titer Adeno-Associated Viral Vectors from a Rep/Cap Cell Line and Hybrid Shuttle Virus," *Human Gene Therapy*, 9:2353-2362 (1998).

Grimm et al., "Novel Tools for Production and Purification of Recombinant Adenoassociated Virus Vectors," *Human Gene Therapy*, 9:2745-2760 (1998).

Halbert et. al., "Successful Readministration of Adeno-Associated Virus Vectors to the Mouse Lung Requires Transient Immunosuppression during the Initial Exposure," *Journal of Virology*, 72:9795-9805 (1998).

Inoue and Russell, "Packaging Cells Based on Inducible Gene Amplification for the Production of Adeno-Associated Virus Vectors," *Journal of Virology*, 72:7024-7031 (1998).

Leppard, "Regulated RNA Processing and RNA Transport during Adenovirus Infection," *Virology*, 8:301-307 (1998).

Mah et al., "Adeno-Associated Virus Type 2-Mediated Gene Transfer: Role of Epidermal Growth Factor Receptor Protein Tyrosine Kinase in Transgene Expression," *Journal of Virology*, 72:9835-9843 (1998).

Matsushita et al., "Adeno-associated virus vectors can be efficiently produced without helper virus," *Gene Therapy*, 5:938-945 (1998).

Ni et al., "Cellular Proteins Required for Adeno-Associated Virus DNA Replication in the Absence of Adenovirus Coinfection," *Journal of Virology*, 72:2777-2787 (1998).

Rendahl et al., "Regulation of gene expression in vivo following transduction by two separate rAAV vectors," *Nature Biotechnology*, 16:757-761 (1998).

Rutledge et al., "Infectious Clones and Vectors Derived from Adeno-Associated Virus (AAV) Serotypes Other Than AAV Type 2," *Journal of Virology*, 72:309-319 (1998).

Salvetti et al., "Factors Influencing Recombinant Adeno-Associated Virus Productions," *Human Gene Therapy*, 9:695-706 (1998).

Song et al., "Sustained secretion of human alpha-1-antitrypsin from murine muscle transduced with adeno-associated virus vectors," *Proc. Natl. Acad. Sci. USA*, 95:14384-14388 (1998).

Teramoto et al., "Factors Influencing Adeno-Associated Virsu-Mediated Gene Transfer to Human Cystic Fibrosis Airway Eptithelial Cells: Comparison with Adenovirus Vectors," *Journal of Virology*, 72:8904-8912 (1998).

Wang et al., "Characterization of Wild-Type Adeno-Associated Viru Type 2-Like Particles Generated during Recombinant Viral Vector Production and Strategies for Their Elimination," *Journal of Virology*, 72:5472-5480 (1998).

Xiao et al., "Production of High-Titer Recombinant Adeno-Associated Virus Vectors in the Absense of Helper Adenovirus," *Journal of Virology*, 72:2224-2232 (1998).

Xiao et al., "Adeno-Associated Virus as a Vector for Liver-Directed Gene Therapy," *Journal of Virology*, 72:10222-10226 (1998).

Boivin et al., "Analysis of Synthesis, Stability, Phosphorylation, and Interacting Polypeptides of the 34-Kilodalton Product to Open Reading Frame 6 of the Early Region 4 Protein of Human Adenovirus Type 5," *Journal of Virology*, 73:1245-1253 (1999).

Clark et al., "Highly Purified Recombinant Adeno-Assoicated Virus Vectors Are Biologically Active and Free of Detectable Helper and Wild-Type Viruses," *Human Gene Therapy*, 10:1031-1039 (1999).

Herzog et al., "Long-term correction of canine hemophilia B by gene transfer of blood coagulation factor IX mediated by adeno-associated viral vector," *Nature Medicine*, 5:53-63 (1999).

Koeberl et al., "Persistent, Therapeutically Relevant Levels of Human Granulocyte Colony-Stimulating Factor in Mice after Systemic Delivery of Adeno-Associated Virus Vectors," *Human Gene Theraphy*, 10:2133-2140 (1999).

Qing et al., "Human fibroblast growth factor receptor 1 is a co-receptor for infection by adeno-associated virus 2," *Nature Medicine*, 5:71-77 (1999).

Ogasawara, Y. et al. "Efficient Production of Adeno-associated Virus Vectors Using Split-Type Helper Plasmids," *Jpn. J. Cancer Res.*, 19:481-483 (1999).

Summerford et al., "$\alpha V\beta 5$ integrin: a co-receptor for adeno-associated virus type 2 infection," *Nature Medicine*, 5:78-82 (1999).

Snyder et al., "Correction of hemophilia B in canine and murine models using recombinant adeno-associated viral vectors," *Nature Medicine*, 5:64-70 (1999).

Ye et al., "Regulated Delivery of Therapeutic Proteins After in Vivo Somatic Cell Gene Transfer," *Science*, 283:88-91 (1999).

* cited by examiner

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: PCR Primer

<400> SEQUENCE: 1
gaagatctgc catgccgggg ttttacgag                              29

<210> SEQ ID NO 2
<211> LENGTH: 32
<212> TYPE: DNA
<213> ORGANISM: Artificial Sequence
<220> FEATURE:
<223> OTHER INFORMATION: PCR Primer

<400> SEQUENCE: 2
cactagctag ccagccatac ctggtttaag tc                          32

COMPOSITIONS AND METHODS FOR EFFICIENT AAV VECTOR PRODUCTION

STATEMENT AS TO RIGHTS TO INVENTIONS MADE UNDER FEDERALLY SPONSORED RESEARCH AND DEVELOPMENT

This work was supported by grant DK47754 from the National Institute of Diabetes and Digestive and Kidney Diseases of the National Institutes of Health. The U.S. Government may have certain rights in the invention.

BACKGROUND OF THE INVENTION

Recent success with adeno-associated virus type 2 (AAV) based vectors have fueled considerable interest in this system for gene therapy applications. AAV vectors have been shown to transduce a variety of tissues including lung (Zeitlin et al., *Gene Ther.* 2:623–631 (1995); Halbert et al., *J. Virol.* 72:9795–9805 (1998)), muscle (Kessler et al., *Proc. Nat'l. Acad. Sci. USA* 93:14082–14087 (1996); Herzog et al., *Proc. Nat'l. Acad. Sci. USA* 94:5804–5809 (1997); Clark et al., *Hum. Gene Ther.* 8:659–669 (1997); Fisher et al., *Nature Med.* 3:306–312 (1997)), liver (Koeberl et al., *Proc. Nat'l. Acad. Sci. USA* 94:1426–1431 (1997); Snyder et al., *Nature Gen.* 16:270–276 (1997); Xiao et al., *J. Virol.* 72:10222–10226 (1998)), brain (Xiao et al., *Brain Res.* 756:76–83 (1997)) and other organs. Expression from tissues transduced with AAV vectors can be long term and potentially therapeutic.

The best characterized genetic disease model for AAV-based gene therapy is a treatment for clotting factor IX deficiency (hemophilia B). Sustained, potentially therapeutic levels of human factor IX (FIX) (up to 2,000 ng/ml) were detected in mice for nine (9) months after transduction with an AAV human FIX vector (Herzog et al., *Proc. Nat'l. Acad. Sci. USA* 94:5804–5809 (1997); Snyder et al., *Nature Gen.* 16:270–276 (1997)). Similar results were obtained after muscle or portal vein injection of an AAV vector containing the canine FIX cDNA in the dog model for hemophilia B, although the circulating levels of canine FIX were substantially lower (approximately 70 ng/ml)(Herzog et al., *Nature Med.* 5:56–63 (1999); Snyder et al., *Nature Med.* 5:64–70 (1999)). Additional disorders being evaluated as targets for AAV-mediated gene therapy include hemoglobinopathies (Rendahl et al., *Nature Biotech.* 16:757–761 (1998); Ye et al., *Science* 283:88–91 (1999)), α-1-antitrypsin deficiency (Song et al., *Proc. Nat'l. Acad. Sci. USA* 95:14384–14388 (1998)), and cystic fibrosis (Flotte et al., *Proc. Nat'l. Acad. Sci. USA* 90:10613–10617 (1993)).

A major obstacle to the realization of the clinical potential for AAV is the effort required to produce sufficient quantities of AAV vectors. This is a particular problem for in vivo applications such as direct delivery to the lung. The dose dependence observed for AAV-derived FIX expression in the dog studies indicated that approximately $10^{13}$ particles/kg weight is required to achieve therapeutic levels of expression (Herzog et al., *Nature Med.* 5:56–63 (1999). The reported yield for current AAV production ranges from $10^2$ to $10^5$ particles per transfected cell (Xiao et al., *J. Virol.* 72:2224–2232 (1998)). Using conventional transfection procedures to generate $10^{13}$ particles would require at least 20 and up to 20,000 10 cm tissue culture plates of, for example, 293 cells.

In addition, the requirement for helper adenovirus infection or transfection of plasmids encoding the adenovirus proteins during AAV vector production introduces potential contaminants in vector stocks (Muzcyzka., *Curr. Top. Microbiol. Immunol.* 158:97–129 (1992); Xiao et al., *J. Virol.* 72:2224–2232 (1998); Matsushita et al., *Gene Ther.* 5:938–945 (1998)). The helper virus activity enables the appropriate expression of the AAV open reading frames during wild type AAV replication and AAV vector production (Muzcyzka, supra, (1992)).

The wild type AAV genome is a 4,600 base single stranded DNA molecule including a terminal 145 base repeat sequence (TR) at each end (Muzcyzka, supra, (1992)). The AAV non-structural and structural open reading frames (orfs) responsible for replication and encapsidation of the genome are derived from alternatively spliced transcripts originating from three distinct promoters. The replication (Rep) proteins are designated as Rep 78/68 and Rep 52/40, initiated at the P5 and P19 promoters, respectively. The structural capsid (Cap) proteins (VP1, VP2, and VP3) are under the control of the P40 promoter (Muzcyzka, supra, (1992)). A combination of the terminal repeats, cis-sequences proximal to the AAV promoters, Rep proteins, adenovirus gene products, and cellular factors are responsible for the appropriate expression of the AAV Rep and Cap proteins (Tratschin et al., *Mol. Cell. Biol.* 6:2884–2894 (1986); Beaton et al., *J. Virol.* 63:4450–4454 (1989); Chang et al., *J. Virol.* 63:3479–3488 (1989); McCarty et al., *J. Virol.* 65:2936–2945 (1991); Shi et al., *Cell* 67:377–388 (1991); Horer et al., *J. Virol.* 69:5484–5496 (1995); Kyostio et al., *J. Virol.* 69:6787–6796 (1995); Lewis et al., *J. Virol.* 69:1628–1636 (1995); Weger et al., *J. Virol.* 71:8437–8447 (1997); Ni et al., *J. Virol.* 72:2777–2787 (1998)).

Adeno-associated virus is a defective parvovirus that grows in cells in which certain functions are provided by a co-infecting helper virus. General reviews of AAV may be found in, for example, Carter, *Handbook of Parvoviruses*, Vol. I, pp. 169–228 (1989), and Berns, *Virology*, pp. 1743–1764, Raven Press, New York, N.Y. (1990), incorporated herein by reference). Examples of co-infecting viruses that provide helper functions for AAV growth and replication are adenoviruses, herpesviruses, and in some cases, poxviruses such as vaccinia. The nature of the helper function is not entirely understood, but it appears that the helper virus indirectly renders the cell permissive for AAV replication. This belief is supported by the observation that AAV replication may occur at low efficiency in the absence of helper virus co-infection if the cells are treated with agents that are either genotoxic or that disrupt the cell cycle.

Although AAV may replicate to a limited extent in the absence of helper virus in these unusual conditions, more generally infection of cells with AAV in the absence of helper functions results in the proviral AAV genome integrating into the host cell genome. If these cells are superinfected with a helper virus such as adenovirus, the integrated AAV genome can be rescued and replicated to yield a burst of infectious progeny AAV particles. The fact that integration of AAV appears to be efficient suggests that AAV would be a useful vector for introducing genes into cells for use, such as, in human gene therapy.

AAV has a very broad host range without any obvious species or tissue specificity and can replicate in virtually any cell line of human, simian or rodent origin provided that an appropriate helper is present. AAV is also relatively ubiquitous and has been isolated from a variety of animal species including most mammalian and several avian species.

AAV is not associated with any known cause of disease. Nor is AAV a transforming or oncogenic virus, and integration of AAV into the genetic material of human cells generally does not cause significant alteration of the growth properties or morphological characteristics of the host cells. These properties of AAV also recommend it as a potentially useful human gene therapy vector because most of the other viral systems proposed for this application, such as retroviruses, adenoviruses, herpesviruses, or poxviruses, are disease-causing.

AAV vectors including heterologous polynucleotide sequences flanked by the AAV terminal repeats (TRs) can be assembled into virions when introduced into appropriate cells by transfection with packaging plasmids encoding the Rep and Cap reading frames, but lacking the TRs, and by co-infection with the non-related helper adenovirus (Samulski et al., *J. Virol.* 63:3822–3828 (1989); Muzcyka, *Curr. Top. Microbiol. Immunol.* 158:97–129 (1992)).

Initial AAV packaging plasmids contained simple deletions of the packaging signal (TRs) to supply the Rep and Cap proteins for AAV vector production without generating wild type virus (Samulski et al., supra, (1989); Muzcyzka, supra, (1992)). The AAV/Ad packaging construct, for example, has been widely used to generate AAV vector stocks by co-transfection into human embryonic kidney 293 cells (Graham et al., *J. Virol.* 36:59–74 (1977); Samulski et al., *J. Virol.* 63:3822–3828 (1989)). A derivative packaging plasmid, ACG-2, was described which converted the Rep 79/68 initiation codon from AUG to ACG to reduce the level of Rep 78/68 expression (Li et al., *J. Virol.* 71:5236–5243 (1987)). Over expression of the Rep 78/68 proteins has been correlated with decreases in AAV vector production. Expression of the AAV reading frames from these plasmids is still dependent upon transcription from the AAV P5, P19, and P40 promoters.

Co-transfection of AAV/Ad and AAV vector plasmids has been shown to result in significant contamination of vector stocks with replication-competent AAV (rcAAV) presumably by recombination between the plasmids during transfection (Allen et al., *J. Virol.* 71:6816–6822 (1997); Salvetti et al., *Hum. Gene Ther.* 9:695–706 (1998); Wang et al., *J. Virol.* 72:5472–5480 (1998)). An AAV packaging plasmid has previously been described which split the AAV rep and cap genes, placing them in an inverted orientation relative to the wild type AAV, and replaced the P5 and P40 promoters with the mouse metallothionein and cytomegalovirus (CMV) regulatory sequences, respectively (MTrep/CMVcap, FIG. 1)(Allen et al., supra, (1997); WO98/27204, each incorporated herein by reference). AAV vector production with this packaging plasmid was comparable to levels of vector produced with the AAV/Ad packaging plasmid and was free of rcAAV. Production of AAV vector using MTrep/CMVcap was still enhanced by infection with helper adenovirus despite the substitution of the P5 and P40 promoter sequences.

Adenovirus infection is an easy and efficient method for supplying the helper activities necessary for AAV vector production. However, removal of adenovirus from AAV vector stocks is laborious and can result in the contamination of vector stocks with potentially immunoreactive adenovirus proteins. Recently it has been shown that the adenovirus activities required for AAV vector production can be supplied by transfection of 293 cells with plasmids containing the E2A, E4 and VA RNA genes (Xiao et al., 72:2224–2232 (1998); Matsushita et al., *Gene Ther.* 5:938–945 (1998)). Full helper activity required the transfection of all three transcription units (Matsushita et al., supra, (1998), incorporated herein by reference).

There are at least two desirable features of any AAV vector designed for use in human gene therapy. First, the transducing vector must be generated at titers sufficiently high to be practicable as a delivery system. This is especially important for gene therapy stratagems aimed at in vivo delivery of the vector. For example, it is likely that for many desirable applications of AAV vectors, such as treatment of cystic fibrosis by direct in vivo delivery to the airway, the required dose of transducing vector may be in excess of $10^{10}$ particles. Secondly, the vector preparations must be essentially free of wild type AAV virus (or any replication-competent AAV). The attainment of high titers of AAV vectors has been difficult for several reasons including preferential encapsidation of wild type AAV genomes (if they are present or generated by recombination), and the difficulty in generating sufficient complementing functions such as those provided by the wild type rep and cap genes. Useful cell lines expressing such complementing functions have been especially difficult to generate, in part because of pleiotropic inhibitory functions associated with the rep gene products. Thus, cells in which the rep gene is integrated and expressed tend to grow slowly or express rep at very low levels.

What is needed in the art is a highly efficient AAV vector production system which produces high titers of recombinant AAV vector and which is free of potentially contaminating wild type AAV virus and helper virus. The present invention provides methods which do not require the addition of a helper virus to obtain high titers of vector by using a vector construct which contains a single open reading frame from a single helper adenovirus gene. The chances of producing a potentially infective viral particle is practically eliminated because only a single gene is used from a helper virus for recombinant AAV vector encapsidation. Vectors of the present invention also provide methods for highly efficient recombinant AAV vector production which fulfill this and other related needs in the art.

SUMMARY OF THE INVENTION

The present invention provides a mammalian cell which can package a recombinant adeno-associated virus (AAV) vector at high efficiency to produce high titers of recombinant AAV vector particles. The cells comprise a polynucleotide sequence encoding an AAV cap gene operably linked to a heterologous promoter, a polynucleotide sequence encoding an AAV rep gene operably linked to a promoter, and a polynucleotide sequence encoding an adenovirus E4orf6 gene. When these packaging cells are transfected with a recombinant vector comprising a polynucleotide of interest positioned between two AAV terminal repeat regions and incubated under conditions conducive to replication and packaging, a recombinant AAV vector comprising the polynucleotide of interest is packaged into a recombinant AAV vector particle.

Promoters which can be operably linked to the AAV rep gene include, but are not limited to, a promoter naturally associated with the AAV rep gene or can be a heterologous promoter. In an optional embodiment of the present invention the heterologous promoter operably linked to the AAV rep and operably linked to the AAV cap genes can be the same. It is typical for the heterologous promoter operably linked to the AAV rep gene to be inducible in order to prevent damage to the transfected or transduced mammalian cell should large amounts of Rep protein be produced. The metallothionein promoter is a preferred inducible promoter, particularly the murine metallothionein I (MT-I) promoter.

The AAV cap gene can be provided operably linked to a heterologous promoter. It is preferred in producing the packaging cells of the present invention to provide a strong promoter to express the AAV cap gene. A cytomegalovirus (CMV) promoter, particularly, the CMV major IE gene promoter, is preferred.

Mammalian packaging cells of the present invention, comprise genes encoding AAV rep and AAV cap in order to provide replication and encapsidation functions for recombinant AAV vector. The genes can be provided on the same plasmid or can be provided as AAV split-packaging genes. It is particularly preferred to provide the polynucleotide sequence encoding the AAV rep gene operably linked to a promoter and the polynucleotide sequence encoding the AAV cap operably linked to a heterologous promoter as separate vectors.

High levels of recombinant AAV vector can be produced by mammalian packaging cells of the present invention comprising AAV rep and AAV cap genes from any AAV serotype. In a particularly preferred embodiment, the present invention provides mammalian cells comprising a polynucleotide sequence encoding AAV type 2 rep and AAV type 2 cap genes or AAV type 6 rep and AAV type 6 cap genes. The rep and cap gene can also be of different AAV types, for example, AAV type 2 cap and AAV type 6 rep or AAV type 6 cap and AAV type 2 rep, and the like.

The mammalian packaging cells of the present invention also comprise a polynucleotide sequence encoding an adenovirus E4orf6 gene which provides the "helper" function necessary to package recombinant AAV vector into a recombinant AAV viral particle. In a particular embodiment of the present invention, the polynucleotide sequence encodes an adenovirus type 5 E4orf6 gene, although other adenovirus E4 open reading frame 6 genes can also be used.

The present invention further provides methods for the production of recombinant AAV vector, comprising the steps of: (a) providing a mammalian cell which can package a recombinant AAV vector into a recombinant AAV viral particle at high efficiency, the cell comprising a polynucleotide sequence encoding an AAV cap gene operably linked to a heterologous promoter, a polynucleotide sequence encoding an AAV rep gene operably linked to a promoter, and a polynucleotide sequence encoding an adenovirus E4orf6 gene; (b) introducing a recombinant vector comprising a polynucleotide of interest positioned between two AAV terminal repeat (TR) regions; and (c) incubating the cell under conditions conducive to replication and packaging of the recombinant AAV vector. Typically, the AAV rep and AAV cap genes are provided as an AAV split-packaging gene. In a particular embodiment the AAV rep and the AAV cap genes are provided as separate vector constructs.

A typical embodiment of the method comprises providing a mammalian packing cell transfected or transformed with a first vector comprising a polynucleotide sequence encoding an AAV rep gene operably linked to a promoter, such as the murine metallothionein I promoter, a second vector comprising a polynucleotide sequence encoding an AAV cap gene operably linked to a heterologous promoter, such as the cytomegalovirus major IE gene promoter; a third vector encoding an adenovirus E4orf6 gene; and a fourth vector comprising a polynucleotide of interest positioned between two AAV terminal repeat (TR) regions. Recombinant AAV vector have been efficiently packaged using polynucleotide sequence encoding various combinations of AAV serotype cap and rep genes including both the AAV serotype 2 rep and AAV serotype 2 cap genes and the AAV serotype 6 rep and AAV serotype 6 cap genes.

Methods are also provided for producing a mammalian cell which can package a recombinant AAV vector at high efficiency comprising: transducing or transfecting a mammalian host cell susceptible to infection by AAV with a first vector comprising a polynucleotide sequence encoding an AAV cap gene operably linked to a heterologous promoter, transducing or transfecting the mammalian cell with a second vector comprising a polynucleotide sequence encoding an AAV rep gene operably linked to a promoter, transducing or transfecting the mammalian cell with a third vector comprising a polynucleotide sequence encoding an adenovirus E4orf6 gene. The transfected or transduced host cell is then grown under conditions conducive for replication and selection of the transduced or transfected mammalian cells comprising polynucleotide sequences encoding an AAV rep gene, an AAV cap gene, and a polynucleotide sequence encoding an adenovirus E4orf6 gene. It is particularly preferred that the mammalian cell be transfected with a vector encoding an adenovirus type 5 E4orf6 gene. Further, it is typical that the mammalian cell be transfected or transduced with vectors comprising a polynucleotide sequence encoding an AAV type 2 rep gene and an AAV type 2 cap gene or that the mammalian cell be transfected with vectors comprising a polynucleotide sequence encoding an AAV type 6 rep gene and an AAV type 6 cap gene. But, combinations of AAV type 2 and AAV type 6 cap and rep genes can also be used. Calcium phosphate precipitation and electoporation are typical methods for transfecting the mammalian cells.

BRIEF DESCRIPTION OF THE DRAWINGS

FIG. 1 depicts maps of various plasmids used herein. Depicted are the infectious plasmid clone for AAV type 2, pSub201; AAV type 2 packaging plasmids ACG-2, MTrep/CMVcap, MTrep, and CMVcap; AAV type 2 vector plasmid ARAP4; and the adenovirus type 5 E4orf6 expression plasmid, CMVE4orf6. Arrows indicate transcriptional start sites. Abbreviations: TR, AAV type 2 terminal repeat; rep, AAV replication open reading frame (orf); cap, AAV type 2 capsid orf; AdTR, adenovirus terminal 107 base pairs; pA, poly adenylation signal; CMV, cytomegalovirus major IE gene promoter; MT, murine metallothioein gene sequences; SV40, simian virus 40 sequence; RSV, Rous sarcoma virus sequence; AP, human placental alkaline phosphatase cDNA; E4orf6, adenovirus type 5 early region 4 orf 6; LTR, retroviral long terminal repeat.

DESCRIPTION OF THE SPECIFIC EMBODIMENTS

Recombinant adeno-associated virus (rAAV) vectors are potentially powerful tools for human gene therapy, particularly for diseases such as cystic fibrosis and sickle cell anemia. A major advantage of rAAV vectors over other approaches to gene therapy is that the rAAV vectors generally do not require ongoing replication of the target cell in order to become stably integrated into the host cell.

The invention described herein provides methods and materials for use in the efficient production of high titers of recombinant AAV vectors. Further provided are compositions for transducing or transfecting airway epithelial cells in vivo at high efficiency compared to those compositions used previously.

The practice of the present invention employs, unless otherwise indicated, conventional techniques of molecular biology, microbiology, recombinant DNA, and immunology, which are within the skill in the art. Such techniques are described fully in the literature. See, for example, Sambrook et al., *Molecular Cloning: A Laboratory Manual*, Second Edition (1989), *Oligonucleotide Synthesis* Gait, ed., (1994), *Animal Cell Culture*, Freshney, ed., (1987), the series *Methods in Enzymology* (Academic Press, Inc.); *Gene Transfer Vectors for Mammalian Cells*, Miller and Carlos, eds. (1987); *Handbook of Experimental Immunology*, 4th Edition, Weir et al., eds., (1986); *Current Protocols in Molecular Biology*, Ausubel et al. eds. (1987); *Current Protocols in Immunology*, Coligan et al. eds. (1991).

Definitions:

The terms "polypeptide", "peptides" and "protein" are used interchangeably to refer to polymers of amino acids of any length. These terms also include proteins that are post-translationally modified through reactions that include, but are not limited to, glycosylation, acetylation and phosphorylation.

"Polynucleotide" refers to a polymeric form of a nucleic acid of any length, either ribonucleotides or deoxyribonucleotides, or analogs thereof. This term refers only to the primary structure of the molecule, the sequence of nucleotides. Thus, double- and single-stranded DNA, as well as double- and single-stranded RNA are included. It also includes modified polynucleotides such as methylated or capped polynucleotides.

A "gene" refers to a polynucleotide, or polynucleotide sequence, containing at least one open reading frame that is capable of encoding a particular protein after being transcribed and translated.

A "transcriptional regulatory sequence" or "TRS" is used herein to refer to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" or "operably associated" refers to an arrangement of two or more components, wherein the components described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to the coding sequence.

"Recombinant" refers to a genetic entity distinct from that generally found in nature. As applied to a polynucleotide or gene, this means that the polynucleotide, or polynucleotide sequence, is the product of combinations of molecular manipulations including, but not limited to, cloning, restriction and/or ligation steps, and other procedures that result in a construct that is distinct from the polynucleotide found in nature.

"Heterologous" means derived from a genotypically distinct entity from that of the rest of the entity to which it is compared. For example, a polynucleotide introduced by genetic engineering techniques into a different cell type is a heterologous polynucleotide. When that polynucleotide is expressed, the polynucleotide can encode a heterologous polypeptide. Similarly, a TRS or promoter that is removed from its native coding sequence and operably linked to a different coding sequence is a heterologous TRS or promoter.

"Sequence overlap" between two polynucleotides occurs when the nucleotides share a identical or substantially identical sequence. When this identity of sequence is of sufficient length and identity, recombination is facilitated. The level of identity and corresponding frequency of recombination increase with increasing length of the sequences and with their level of shared identity. The level of identity that may pose a concern in a given system can be determined theoretically and confirmed experimentally, as is known in the art. For example, recombination can be substantially reduced or eliminated if the two sequences do not share any stretch of at least 20 base pairs (bp) that is generally greater than about 80% identity (summed over its length), or any stretch of at least 20 bp that is at least 70% identity, or any stretch of at least 50 bp that is at least 50% identity, or any stretch of at least about 100 bp that is at least 40% identity; preferably the levels of identity are even less (preferably less than half of the stated levels), and preferably the lengths of partially homologous sequences are also less (preferably less than half the stated lengths).

A "vector" as used herein refers to a recombinant plasmid or virus that comprises a polynucleotide to be delivered into a host cell, either in vitro or in vivo. The polynucleotide to be delivered, sometimes referred to as a "target polynucleotide" or "transgene", can comprise a coding sequence of interest in, for example, gene therapy, and/or a selectable or detectable marker.

A "replicon" refers to a polynucleotide comprising an origin of replication which allows for replication of the polynucleotide in an appropriate host cell. Examples of replicons include, but are not limited to, episomes (including plasmids and the like), as well as chromosomes, i.e., the nuclear or mitochondrial chromosomes.

"Stable integration" of a polynucleotide into a cell means that the polynucleotide has been integrated into a replicon that tends to be stably maintained in the cell. Although episomes such as plasmids can sometimes be maintained for many generations in a host cell, genetic material carried episomally is generally more susceptible to loss than chromosomally-integrated material. However, maintenance of a polynucleotide can often be effected by incorporating a selectable marker into or adjacent to a polynucleotide, and then maintaining cells carrying the polynucleotide under selective pressure.

In some cases, sequences cannot be effectively maintained stably unless they become integrated into a chromosome; and therefore, selection for retention of a sequence comprising a selectable marker can result in selection of a cell in which the marker has become stably-integrated into a chromosome. Antibiotic resistance genes can be conveniently employed in this regard, as is well known in the art. Typically, stably-integrated polynucleotides would be expected to be maintained on average for at least about twenty generations, preferably at least about one hundred generations, still more preferably they would be maintained permanently. The chromatin structure of eukaryotic chromosomes can influence the level of expression of an integrated polynucleotide. Having the genes carried on episomes can be particularly useful where having multiple stably-maintained copies of a particular gene is desired.

"AAV" is a standard abbreviation for adeno-associated virus. Adeno-associated virus is a single-stranded DNA parvovirus that grows only in cells in which certain functions are provided by a co-infecting helper virus. There are currently six serotypes of AAV that have been characterized. General information and reviews of AAV can be found in, for example, Carter, 1989, *Handbook of Parvoviruses*, Vol. 1, pp. 169–228, and Berns, 1990, *Virology*, pp. 1743–1764, Raven Press, (New York). The type 2 and type 6 serotypes have been used to illustrate the present invention in the Examples provided herein below. However, it is fully expected that these same principles will be applicable to additional AAV serotypes since it is well known that the various serotypes are quite closely related, both structurally and functionally, even at the genetic level. (See, for example, Blacklowe, 1988, pp. 165–174 of *Parvoviruses and Human Disease*, J. R. Pattison, ed.; and Rose, *Comprehensive Virology* 3:1–61 (1974)). For example, all AAV serotypes apparently exhibit very similar replication properties mediated by homologous rep genes; and all bear three related capsid proteins such as those expressed in AAV 2 and AAV 6. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. The type 2 and type 6 serotypes of AAV have been used to construct similar packaging cells with comparable levels of recombinant AAV vector production.

The high degree of relatedness between the AAV serotypes presents the possibility of producing vector particles that are pseudotyped with different AAV serotype capsids. Within one example, AAV 2 vectors and AAV 6 vectors can be serotyped with AAV6 capsid using either AAV 6 rep and AAV 6 cap or AAV 2 rep and AAV 6 cap. As discussed in more detail herein, it has been demonstrated that such AAV 6 serotyped vector showed preferential transduction into distal airway epithelium and bronchial epithelium relative to AAV 2 and AAV 6 serotyped vectors.

A "recombinant AAV vector" (or "rAAV vector") as used herein refers to a vector comprising one or more polynucleotides of interest (or transgenes) that are flanked by AAV terminal repeat sequences (TRs). Such rAAV vectors can be replicated and packaged into infectious viral particles when present in a host cell that has been transfected with a vector encoding and expressing rep and cap gene products, i.e., AAV Rep and Cap proteins, and wherein the host cell has been transfected with a vector which encodes and expresses a protein from the adenovirus open reading frame E4orf6. When a rAAV vector is incorporated into a larger polynucleotide, e.g., in a chromosome or in another vector such as a plasmid used for cloning or transfection, then the rAAV vector is typically referred to as a "pro-vector". The pro-vector can be "rescued" by replication and encapsidation in the presence of AAV packaging functions and necessary helper functions provided by E4orf6.

"Packaging" as used herein refers to a series of subcellular events that results in the assembly and encapsidation of a viral vector, particularly an AAV vector. Thus, when a suitable vector is introduced into a packaging cell under appropriate conditions it can be assembled into a viral particle. Functions associated with packaging of viral vectors, particularly AAV, are described herein and in the art. AAV 2 vector (vector2) denotes the assembly and encapsidation of a recombinant AAV vector comprising a polynucleotide of interest flanked by AAV 2 terminal repeat sequences. AAV 6 vector (vector6) denotes the assembly and encapsidation of a recombinant AAV vector comprising a polynucleotide of interest flanked by AAV 6 terminal repeat sequences.

AAV "rep' and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." Modified AAV packaging genes, including modified rep genes and modified cap genes, are described below. Typically, in a method of the present invention the rep and cap transcription units are provided as two separate plasmids relative to single AAV packaging plasmids. Presentation on separate plasmids apparently improves the function of the heterologous promoters to initiate transcription of the operably associated polynucleotide.

Within one embodiment of the invention, AAV 6 rep and AAV 6 cap genes are used to package a recombinant AAV vector containing AAV TRs derived from the AAV 2 serotype virus. Within another embodiment an AAV 2 rep gene and an AAV 6 cap gene are used to package a recombinant AAV vector containing AAV TRs derived from the AAV 2 serotype virus.

An "AAV split-packaging gene" refers to a recombinant gene encoding one or more AAV packaging proteins, including AAV Rep proteins and/or AAV Cap proteins, wherein the split-packaging gene has been separated from one or more AAV packaging genes to which it is normally linked in the AAV genome. Examples of split-packaging genes include AAV split-cap genes, AAV split-rep78 genes and AAV split-rep52 genes, as described in WO98/27204 (incorporated herein by reference). The split-packaging gene, or genes, can be operably linked to a heterologous promoter.

An AAV "split-cap" gene refers to a recombinant gene encoding one or more AAV Cap proteins, which gene is separated from Rep-specific sequences of an AAV rep gene, i.e., rep78. The split-cap gene is operably linked to a promoter, preferably a heterologous promoter. The wild-type AAV rep gene contains two promoter sequences, p15 and p19, which drive the expression of the "large Rep: proteins (Rep78 and Rep68) and the "small Rep" proteins (Rep52 and Rep40), respectively. The wild-type AAV cap gene contains a promoter, p40, which drives the expression of the AAV Cap proteins (VP1, VP2, and VP3). AAV cap genes can also be obtained from non-human adeno-associated viruses, as described in WO95/20671 (incorporated herein by reference). The Cap proteins can be encoded by a split-cap gene which, unlike the situation in wild-type AAV, is not located next to a gene which encodes the large Rep proteins. Rather, an AAV "rep78" gene (a gene which encodes the large Rep proteins Rep78 and Rep68) is provided separately, in a different location. The split-cap genes can be physically separated from Rep78-specific sequences by being present on different replicons or vectors, or, if present on a single replicon or vector, by being separated from Rep78-specific sequences by intervening non-AAV DNA. A split-cap gene can be operably linked to a heterologous promoter, i.e., a promoter other than the AAV P40 promoter, which heterologous promoter is incorporated upstream of the split-cap coding region, either in place of or in addition to the P40 promoter.

An AAV "rep78" gene is a gene which encodes the large Rep proteins Rep78 and Rep68. Generally, the gene will also encode the small Rep proteins Rep52 and Rep40. The rep 78 gene can be operably linked to a heterologous promoter, i.e., a promoter other than the AAV P5 promoter, which heterologous promoter is incorporated upstream of the rep 78 coding region, either in place of, or, in addition to the P5 promoter.

An AAV "rep52" gene can separately encode just the small Rep proteins Rep 52 and Rep40. A rep52 gene of the present invention is operably linked to a heterologous promoter, i.e., a promoter other than the AAV P19 promoter, which heterologous promoter is incorporated upstream of the rep52 coding region, either in place of, or, in addition to the P19 promoter. An AAV split-cap gene, rep52 gene and/or rep78 gene can also be operably linked to other transcriptional regulatory sequences, including enhancers and polyadenylation (polyA) sequences, which additional TRSs can also be heterologous. AAV-derived split-cap genes, rep52 and rep78 genes as described herein are collectively referred to as "AAV split-packaging genes."

As used herein "E4orf6" refers to a polynucleotide sequence encoding an Adenovirus early region 4 orf 6 gene. In a particular embodiment of the present invention the E4orf6 gene from adenovirus type 5 has been used to provide helper virus functions for the assembly of infectious rAAV. It should be understood by the skilled artisan that other homologous genes from other types of Adenovirus can be used in the methods of the present invention to substitute for E4orf6 of type 5 Adenovirus.

A "terminator" refers to a polynucleotide sequence that tends to diminish or prevent read-through transcription, i.e., diminishes or prevents transcription originating on one side of the terminator from continuing through to polynucleotide sequence at the other side of the terminator. Examples of a terminator useful in the present invention comprises a poly A sequence, one or more stop codons, and the like.

"Efficiency" when used in describing a cell line refers to certain useful attributes of the cell line. In particular, the growth rate, and, for packaging cell lines, the number of virus particles produced per cell. "High efficiency packaging" refers to production of at least 100 viral particles per cell, more preferably at least about 200 viral particles per cell, still more preferably at least about 400 viral particles per cell. "High safety packaging" indicates that, of the recombinant AAV viral particles produced, fewer than about 1 in $10^6$ are replication-competent AAV (rcAAV) viral particles, preferably fewer than about 1 in $10^8$ are replication competent, more preferably fewer than about 1 in $10^{10}$ are replication competent, most preferably none of the viral particles produced are replication competent.

Host cells, cell lines, cell culture, packaging cells and other such terms describe higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical, in, for example, morphology or in genomic complement, to the original parental cell.

A "therapeutic gene", "target polynucleotide", "transgene", "gene of interest" and the like generally refer to a gene or genes to be transferred using a vector, i.e., a heterologous gene. Typically, in the context of the present invention, such genes are located within the recombinant Adeno-associated virus (rAAV) vector, which vector is flanked by terminal repeat (TR) regions and therefore can be replicated and encapsidated into rAAV particles. Target polynucleotides can be used in this invention to generate rAAV vectors for a number of different applications. Such polynucleotides include, but are not limited to, (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators, such as cytokines; (v) polynucleotides that can make recipient cells susceptible to specific drugs, such as the herpes virus thymidine kinase gene, and the like; and (vi) polynucleotides for the treatment of various cancers.

To effect expression of the transgene in a recipient host cell, it is generally operably linked to a promoter, either its own or a heterologous promoter. A large number of suitable promoters are known in the art, the choice of which depends on the desired level of expression of the transgene; whether one wants constitutive expression, inducible expression, cell-specific or tissue-specific expression, and the like. The rAAV vector can also contain a selectable marker.

The method for producing high titers of recombinant AAV vectors comprises several steps. The general strategy comprises preparation of mammalian packaging cells that comprise a polynucleotide encoding an AAV cap gene operably linked to a heterologous promoter; a polynucleotide encoding an AAV rep gene operably linked to a heterologous promoter; and a polynucleotide encoding an adenovirus E4orf6 gene operably linked to a heterologous promoter. Packaging cells are then infected or transfected with a plasmid comprising the AAV inverted terminal repeat regions positioned on either side of a polynucleotide encoding a gene of interest. Under suitable conditions expression of the rep, cap, and E4orf6 genes of the packaging cell results in the synthesis of the Rep, Cap, and E4orf6 proteins which mediate replication and encapsidation of the recombinant AAV vector. Providing a polynucleotide which encodes a gene of interest between the AAV ITR sequences of the recombinant AAV (rAAV) vector results in packaging of the polynucleotide of interest into an infectious rAAV particle which can be used to deliver the gene of interest to a desired host cell.

By providing only a single gene from adenovirus required to "help" AAV vector production the recombinant AAV produced will have the fewest number of potentially immunogenic contaminating adenovirus proteins. Further, the recombinant AAV vector stock produced will not be contaminated with potentially infectious adenovirus eliminating the need for further purification and decontamination of the viral stocks. The methods provided enables the efficient production of rAAV preparations that are of high titer and are free of any contaminating wild-type AAV.

Although the principles of the present invention have been performed with a single serotype of AAV, AAV 2, and an E4orf6 gene from a single adenovirus type, it is expected that these same principles will be applicable to other AAV serotypes and adenovirus serotypes since it is known that the various serotypes of each virus are closely related, respectively.

The parental cell lines from which packaging cells are generated can be obtained from any cell line that is susceptible to AAV infection, and which is amenable to culture in vitro. AAV has a broad host range and has been isolated from a variety of mammalian cell types, including simian, human, and rodent cells. For human gene therapy, human cell lines are typically preferred. Examples of human cell lines from which packaging cells can be derived include, but are not limited to, HeLa (ATCC CL-2), A549 (ATCC CCL-185), 293 (ATCC CRL-1573), KB (ATCC CCL-17), Detroit (various cell line derivatives, i.e., ATCC CCL-54), and WI 38 (ATCC CCL-75), all of which can be obtained from the American Type Culture Collection, 10801 University Boulevard, Manassas, Va. 20110.

In constructing the packaging cell of the present invention, the parental cells are transfected or transformed with a vector comprising polynucleotides which encode the AAV rep gene operably linked to a promoter. Any heterologous promoter can be used as long as it is not strongly down-regulated by rep or cap gene expression. Inducible promoters are preferred because constitutive expression of, in particular, the rep gene can have a negative impact on the host cell. A large variety of inducible promoters are known in the art, including, by way of illustration, heavy metal ion inducible promoters, i.e., metallothionein promoters; steroid hormone inducible promoters, i.e., the MMTV promoter or growth hormone promoters; and promoters such as those from T7 phage which are active in the presence of T7 RNA polymerase. Efficiency of transcription or translation of the AAV rep gene can also be modulated by, for example, alterations in the sequence up stream of the rep gene to decrease the efficiency of transcription of the rep gene, or the coding region can be modified to reduce the efficiency of translation, i.e., mutation of the codon for the initiating methionine can be mutated from ATG to ACG to encode threonine.

In the methods of the present invention, the packaging cell also is transformed or transfected with a vector comprising a polynucleotide sequence encoding an AAV cap gene operably linked to a heterologous promoter. In one embodiment of the present invention, the AAV rep and cap genes are provided on the same vector each with a separate promoter and separated by non-AAV DNA sequence, designated herein as a split-gene plasmid. The promoter operably linked to the AAV rep and the promoter operably linked to the AAV cap gene can be a heterologous promoter and can either be the same heterologous promoter or different. Further, it is preferred that the promoter operably linked to the AAV cap gene be a highly efficient promoter, which can be, but does not necessarily need to be, inducible.

Although recombinant AAV vector is produced at a comparable level using the same rep/cap gene construct with "helper" virus, a 20-fold increase in recombinant AAV vector production can be obtained using two vectors separately comprising the rep gene and the cap gene and their respective operably linked heterologous promoters.

The methods of the present invention also comprise transfection of the parental cell with a vector comprising a polynucleotide sequence which encodes an adenovirus early gene 4 open reading frame 6 (E4orf6) operably linked to a heterologous promoter. In a particular embodiment of the present invention the E4orf6 of adenovirus type 5 is used operably linked with a CMV promoter. This single gene from adenovirus provides all of the "helper" functions necessary for highly efficient replication and encapsidation of recombinant AAV vector particles. In a preferred embodiment of the present invention the packaging cell produced recombinant AAV vector particles at a level twenty fold above that of a previously used packaging cells using "helper" virus co-infection.

To generate recombinant AAV particles which can be useful in, for example, gene therapy, the packaging cell is provided with a recombinant AAV vector comprising AAV terminal repeat (TR) regions on either side of one or more polynucleotides which encode a gene of interest, or "target" polynucleotide. TR regions of any of the serotypes of AAV can be used, including for example, those from AAV 2 or AAV 6 and the like. In a particularly preferred embodiment of the present invention the terminal repeat regions are inverted. The target polynucleotide, or gene of interest, is preferably operably linked to a promoter. The promoter can be that naturally associated with the gene of interest or can be a heterologous promoter. A large number of suitable promoters are well known in the art. Which promoter is chosen depends on the desired level of expression of the target gene; whether constitutive expression of the polynucleotide is desired, or whether inducible, cell- or tissue-specific expression is desired.

Preferably, the rAAV vector will also contain a positive selectable marker in order to allow for selection of cells that have been infected by the rAAV vector. Negative selectable markers can also be included as a means for selecting against those same cells should that become necessary or desirable. In a preferred embodiment, a "bifunctional selectable fusion gene, such as that described in PCT/US91/08442 and PCT/US94/05601 (incorporated herein by reference), can be used. Briefly, those constructs comprise direct translational fusions between a dominant positive selectable marker and a negative selectable marker. Preferred positive selectable markers are derived from genes selected from hph, neo and gpt, and preferred negative selectable markers can be derived from genes selected from cytosine deaminase, HSV-I, TK, VZV TK, HPRT, APRT, gpt, and the like.

The present invention has been illustrated with a rAAV vector comprising the polynucleotide sequence encoding the gene for human placental alkaline phosphatase to demonstrate the applicability of the invention. The methods and materials provided herein can be used for the production of rAAV vector particles comprising a polynucleotide encoding any gene of interest. Useful genes of interest that can be used to produce rAAV vectors using the methods of the present invention include, but are not limited to, (i) polynucleotides encoding proteins useful in gene therapy, such as to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make a recipient cell susceptible to specific drugs; and (vi) polynucleotides for cancer therapy.

Because the therapeutic specificity of the resulting recombinant AAV vector is determined by the plasmid introduced, the same packaging cell can be used for any of these applications. The plasmid comprising the specific target polynucleotide can be introduced into the packaging cell for production of recombinant AAV vector by any one of a number of methods well known in the art including, calcium phosphate precipitation and electroporation.

The following examples are offered by way of illustration, not by way of limitation.

EXAMPLES

Materials and Methods

Cell Culture. 293 (Graham et al., *J. Virol.* 36:59–74 (1977), incorporated herein by reference); IB3 (Zeitlin et al., *Am. J. Respir. Cell Mol. Biol.* 4:313–319 (1991), incorporated herein by reference), and HT-1080 (American Type Culture Collection (ATCC) CCL 121) were maintained in Dulbecco's modified Eagle medium supplemented with 10% heat-inactivated (30 min at 56° C.) fetal bovine serum, 100 U of penicillin per ml, and 100 µg streptomycin per ml at 37° C. in a 5% $CO_2$-air atmosphere.

Plasmid Construction. The pSub201 (Samulski et al., *J. Virol.* 61:3096–3101 (1987), incorporated herein by reference), ACG-2 (Li et al., *J. Virol.* 71:5236–5243 (1997), incorporated herein by reference), and MTrep/CMVcap (Allen et al., *J. Virol.* 71:6816–6822 (1997), incorporated herein by reference) plasmids have been previously described and contain AAV2-derived gene components. The CMVE4orf6 sequence was isolated on a BamHI/ApaLI fragment from pLNCX-ORF6 (Scaria et al., *Gene Ther.* 2:295–298 (1995), incorporated herein by reference) and cloned into the BamHI/HincII restriction sites in pUC18. The MTrep and CMVcap plasmids were intermediates in the construction of MTrep/CMVcap and contain the identical gene sequences.

The CMVcap6 plasmid was constructed by digesting the CMVcap plasmid with NheI and BglII to liberate the AAV2 capsid encoding fragment and the vector-containing fragment. Plasmid pRepCap6 (Rutledge et al., *J. Virol.* 71: 309–319 (1998); which is incorporated herein by reference in its entirety was digested with Ecl136 to isolate the fragment containing the AAV6 cap sequences. The NheI-BglII vector-containing fragment was ligated to the Ecl136 fragment to generate CMVcap6.

The MTrep6 plasmid was generated by PCR amplification of AAV6 rep sequences from pRepCap (Rutledge et al., supra (1998)) using primers 5' GAAGATCTGC CATGC-CGGGGTTTTACGAG 3' (SEQ ID NO: 1), which contained a BglII linker sequence, and 5'CACTAGCTAGCCAGC-CATACCTGGTTTAAGTC 3' (SEQ ID NO: 2), which contained an NheI linker sequence. The resulting amplicon was digested with BglII and NheI to generate a fragment containing the AAV6 rep.

Plasmid MTrep was digested with BglII and NheI to isolate the vector containing fragment. The BglII-NheI PCR amplicon was ligated to the vector-containing fragment to generate MTrep6.

ARAP4 contains the human placental alkaline phosphatase (AP) cDNA driven by the Rous sarcoma virus regulatory sequences and followed by the SV40 polyadenylation signal flanked by AAV 2 TR sequences inserted into the XbaI sites of pSub201. ARAP4 plasmid was propagated in the SURE bacterial strain (Stratagene).

ARAP4(6) was constructed by isolating the expression cassette driven by the RSV promoter/enhancer, human placental alkaline phosphatase cDNA and the SV40 polyadenylation sequences by digestion of ARAP4 with SnaBI. The DNA fragment was ligated into pA6LAPSN (Rutledge et al., supra (1998)) previously digested with BglII and NheI to release a similar expression cassette but containing the MLV promoter/enhancer and replacing the AAV 2 TR sequences with the TR sequences of AAV 6.

AAV Vector Production. ARAP4 vector stocks were generated as previously described with the following modifications (Koeberl et al., *Hum. Gene Ther.* 10:2133–2140 (1999), incorporated herein by reference). Briefly, cleared lysates were generated from transfected 293 cells 60 to 72 hours after transfection by 3 cycles of freeze/thaw and centrifugation to pellet cell debris. The vector preparation was then pelleted by centrifugation through 40% sucrose and resuspended in Ringer's solution. The transfected 293 cells in the large-scale production of ARAP4 vector were harvested in 10% of the culture medium and purified by CsCl gradient ultracentrifugation as previously described without concentration on a hollow fiber concentrator (Koeberl et al., *Hum. Gene Ther.* 10:2133–2140 (1999), incorporated herein by reference).

ARAP4 Vector Characterization. ARAP4 vector titers were determined by counting AP positive foci after transduction of IB3 or HT-1080 cells (Halbert et al., *J. Virol.* 69:1473–1479 (1995), incorporated herein by reference). Vector particle numbers were determined by Southern blot analysis of purified vector genomes from DNase-treated particles. Vector particles resuspended in Ringer's solution were digested with 10 U of DNase (Stratagene) for 15 min at 37° C. and the DNA was isolated by proteinase K (100 µg/ml) digestion of the virions in SET buffer (1% SDS, 10 mM Tris-pH 7.5, 10 mM EDTA) for 1 hour at 50° C., followed by phenol/chloroform extraction, ethanol precipitation and gel electrophoresis of vector DNA. Replicative form intermediate DNA was purified by proteinase K/SET treatment of cell pellets after freeze/thaw and centrifugation of transfected cells, as described above. Replication-competent AAV contamination of vector stocks was evaluated by replication center assay (Koeberl et al., supra, (1997)).

ARAP4 Vector Delivery to Mouse Airway. C57BL/6 (B6) mice were obtained from Jackson Laboratories (Bar Harbor, Me.). Animals received vector by nasal aspiration in three doses over three days. The lungs were excised and stained for alkaline phosphatase expression one month after inoculation. The transduction efficiency was determined as previously described (Halbert et al., *J. Virol.* 72:9795–9805 (1998), incorporated herein by reference).

Results:

Transcription from the AAV P5, P19, and P40 promoters during transfection or wild type AAV infection was very low in the absence of adenovirus (Loughlin et al. *J. Virol.* 60:515–524 (1986); Muzcyzka, *Curr. Top. Microbiol. Immunol.* 158:97–129 (1992)). Upon infection with adenovirus, transcription from all 3 AAV promoters was elevated in a process requiring the E1A, and E2 proteins (Richardson and Westphal, *J. Virol.* 51:404–410 (1984); Chang et al., *J. Virol.* 63:3479–3488 (1989); Chang and Shenk *J. Virol.* 64:2103–2109 (1990), incorporated herein by reference). Substitution of the constituitively active MT and CMV regulatory sequences for P5 and P40 promoter sequences in MTrep/CMVcap were evaluated to determine if they could enable AAV vector production in the absence of adenovirus infection. ACG-2, a packaging plasmid (FIG. 1) was included as a control for all vector production methods.

Figure 1:
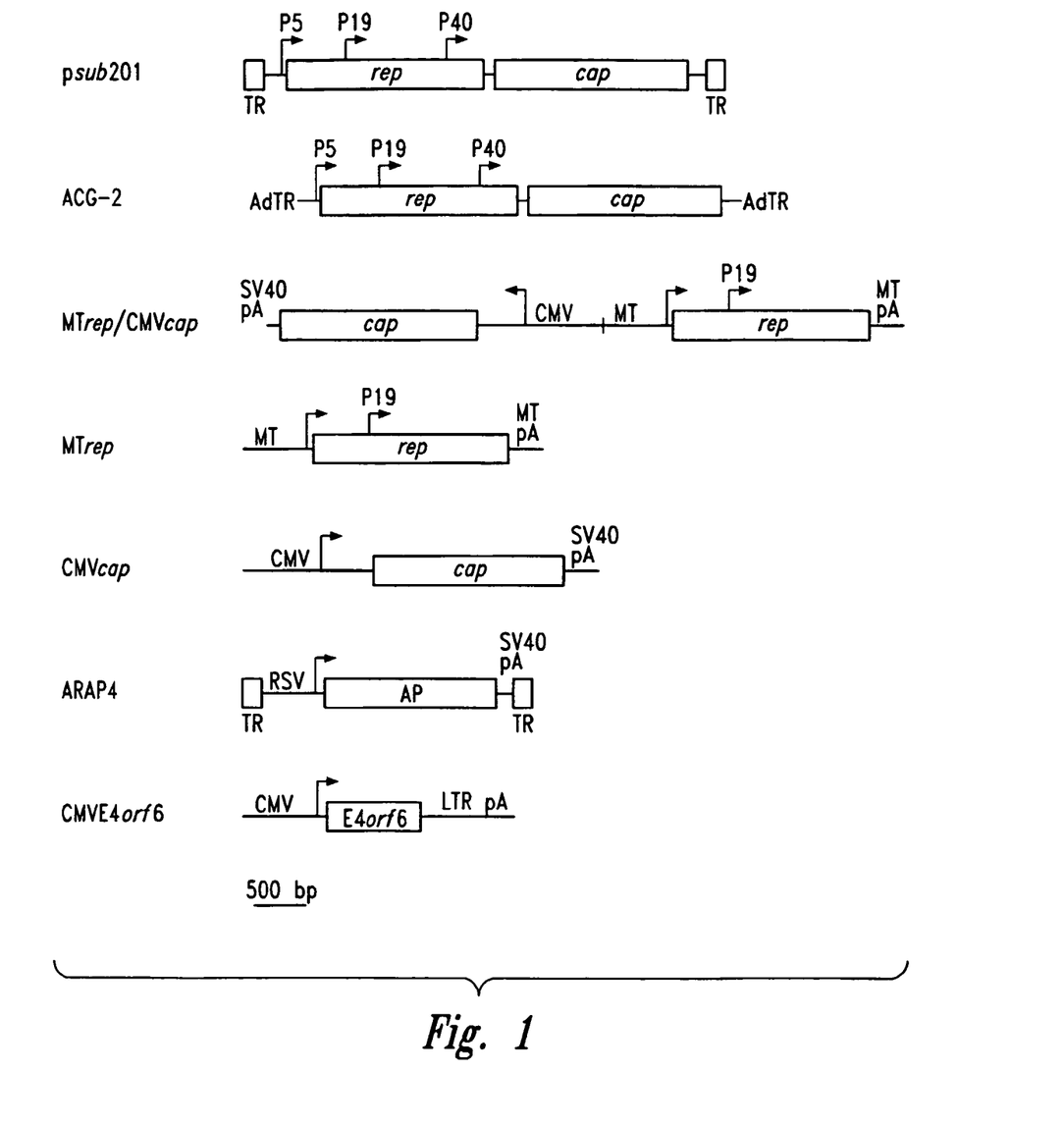
Figure 2:
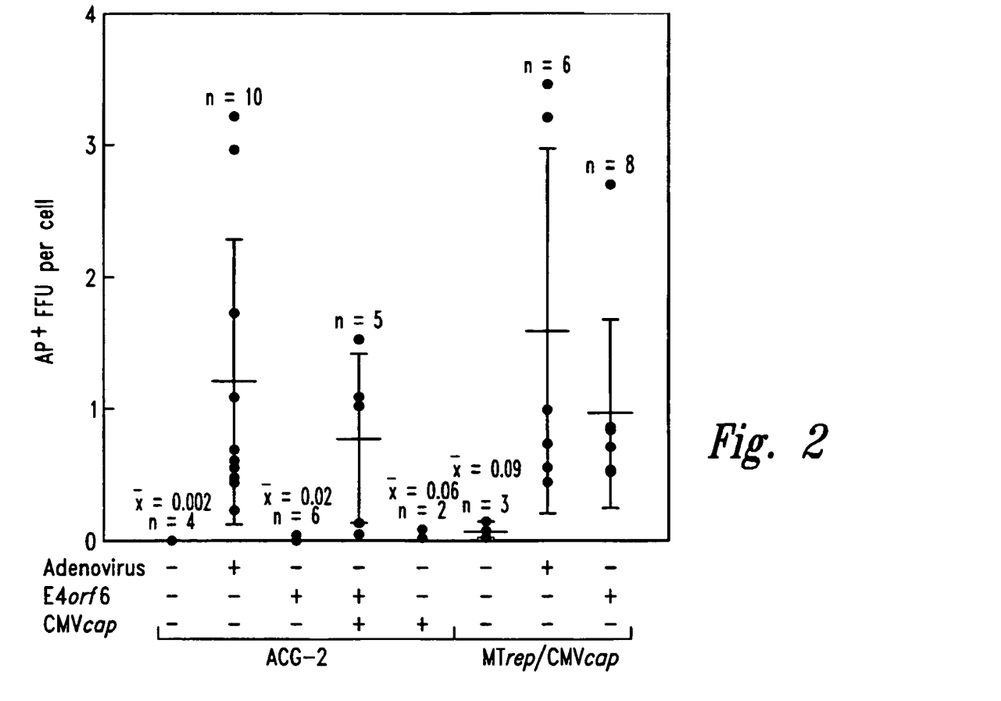
FIG. 2 depicts a comparison of AAV vector (ARAP4) production using the ACG-2 or MTrep/CMVcap AAV packaging plasmids in the presence or absence of adenovirus infection. Where indicated, the adenovirus E4orf6 and CMVcap plasmids were included in the transfections. The transducing titer was determined by exposure of IB3 cells to serial dilutions of vector stocks in the absence of adenovirus infection, followed by staining for alkaline phosphatase activity 3 days after infection. Means (bars)±standard deviations and individual values (solid circles) are shown.

Calcium phosphate mediated transfection of 293 cells with the AAV vector ARAP4 (FIG. 1) and either ACG-2 or MTrep/CMVcap resulted in similar AAV vector production in the presence of adenovirus infection (1.2 and 1.6 AP$^+$ focus forming units (FFU) per transfected cell, respectively) (FIG. 2). As expected, little vector was generated with the ACG-2 packaging plasmid in the absence of adenovirus infection (approximately 0.002 AP$^+$ FFU per cell)(FIG. 2). In contrast, adenovirus-free production with MTrep/CMVcap was approximately 6% of that observed with adenovirus infection (FIG. 2). These results demonstrate that the promoter substitutions in MTrep/CMVcap partially alleviated the helper dependence of AAV production, but implied that additional, post-transcriptional helper activities may be required for maximal yields.

Many adenovirus proteins affect viral and/or cellular protein levels post-transcriptionally, including E2A, VA RNA, and E4 gene products (Jay et al., *Proc. Nat'l. Acad. Sci. USA* 78:2927–2931 (1981); West et al., *Virology* 160: 3847 (1989); Sandler and Ketner, *J. Virol.* 63:624–630 (1980); Nordqvist et al., *Mol. Cell. Biol.* 14:437–445 (1994); Leppard, *J. Gen. Virol.* 78:2131–2138 (1997); Leppard, *Sem. Virol.* 8:301–307 (1998); Boivin et al., *J. Virol.* 73:1245–1253 (1999)). The present invention was intended to test whether a subset of these activities could enable full, adenovirus-free productivity with MTrep/CMVcap. The addition of an E4orf6 expression cassette, CMVE4orf6 (FIG. 1) during AAV vector production with MTrep/CMVcap resulted in the same yield as that observed with adenovirus infection (FIG. 2). In contrast, helper-free vector production was very low with the ACG-2+E4orf6 cotransfection (FIG. 2).

The low level of vector production with ACG-2+E4orf6 in the absence of adenovirus prompted the evaluation of whether Rep and/or Cap activities were absent under these conditions. ARAP4 replication mediated by Rep was monitored by Southern blot analysis of replicative form (RF) intermediates generated after transfection. Total genomic DNA was isolated from post-freeze/thaw cell pellets, the samples were digested with DpnI endonuclease to cut residual plasmid DNA and after transfer, the blot was probed with a $^{32}$P-labeled AP probe. Transfection controls included supplementing the ACG-2+E4orf6 transfections with either the MTrep and/or CMVcap plasmids (FIG. 1). Replicative intermediates were observed in all cases except in the absence of adenovirus or E4orf6. These results demonstrate that the E4orf6 protein is necessary and sufficient for AAV vector replication when using the ACG-2 packaging plasmid. The lack of transducing virion formation under these conditions suggested that capsid production was limiting.

A measure of capsid formation is the ability to protect viral genomes from DNase digestion. Crude supernatants from the ACG-2+E4orf6 transfected cells described above were purified as described in the Materials and Methods. After DNase digestion, viral genomic DNA was isolated and subjected to Southern blot analysis. A strong signal was observed in samples derived from ACG-2 plus adenovirus or MTrep/CMVcap+E4orf6 transfections. As expected, no hybridization was detected from the ACG-2+E4orf6 transfection, but packaged vector was detected when the CMVcap construct was added. Assay of the ARAP4 vector preparations generated using these conditions confirmed that these DNase-resistant virions were capable of transducing IB3 cells (FIG. 2). These results demonstrate that P40-dependent capsid expression from ACG-2 requires additional helper activities not supplied by transfection of the E4orf6 plasmid.

Figure 3:
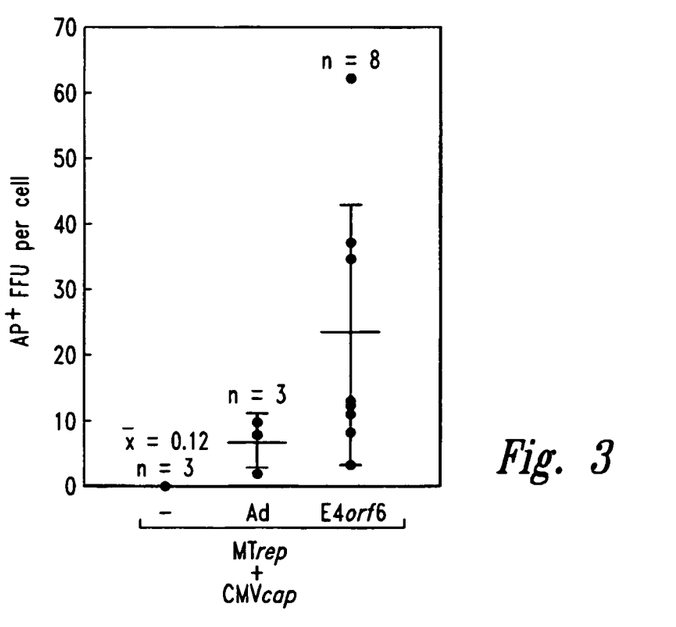
FIG. 3 depicts ARAP4 vector production using the separate MTrep and CMVcap packaging plasmids in the presence or absence of infection with adenovirus or CMVE4orf6 transfection.

The MTrep/CMVcap packaging plasmid was designed to reduce or eliminate the generation of rcAAV during production (Allen et al., supra (1997)). However, the juxtaposition of the MT and CMV regulatory sequences in MTrep/CMVcap could limit capsid expression and vector yield. To test this hypothesis, separate MTrep and CMVcap plasmids were substituted for MTrep/CMVcap in the procedure for ARAP4 vector preparation. Cotransfection of equal amounts of the MTrep and CMVcap plasmids resulted in the highest vector yield. Vector production in the presence of adenovirus infection increased approximately five-fold relative to that observed with MTrep/CMVcap or ACG packaging plasmids (FIGS. 2 and 3). A dramatic increase in vector production (greater than 20-fold) was observed when compared to the single MTrep/CMVcap construct when supplied with the E4orf6 protein instead of infection with adenovirus (FIGS. 2 and 3). These data are consistent with the hypothesis that capsid expression from the CMV promoter is limited upon transfection of a MTrep/CMVcap vector construct.

To determine whether the helper-free AAV vector preparations of the present invention retained full biological activity in vivo, a large preparation of ARAP4 vector was generated. Briefly, 208 10 cm tissue culture plates of 293 cells were transfected with 5 µg each of the MTrep, CMVcap, ARAP4, and CMVE4orf6 plasmids by calcium phosphate transfection and vector virions were purified by CsCl centrifugation (Koeberl et al., *Hum. Gene Ther.* 10:2133–2140 (1999), incorporated herein by reference). Overall production was approximately 10$^4$ DNase resistant particles per cell with a particle to infectivity ratio of about 100, as determined by genome quantitation using Southern blot analysis and adenovirus-free assay of the vector stock on HT-1080 target cells. It should be noted that HT-1080 cells typically display 5 to 10 fold higher transduction relative to IB3 cells for AAV2 vectors. This vector stock was free of replication competent AAV (<1 IU rcAVV per 4×10$^8$ AP$^+$ FFU) by replication center assay (Koeberl et al., *Proc. Natl. Acad. Sci USA* 94:1426–1431 (1997)).

Mice were given 10$^{10}$ AP$^+$ FFU (approximately 10$^{12}$ genome-containing particles) by nasal aspiration and one month later their lungs were analyzed for AP expression as described (Halbert et al., *J. Virol.* 72:9795–9805 (1998), incorporated herein by reference). The lungs exhibited dramatic AP-staining of alveolar cells and vascular smooth muscle cells relative to control animals. There was also an increase in AP-staining of the airway epithelium such that up to 20% of some airways were positive.

Previously, for a dose of approximately 5×10$^8$ AP$^+$ FFU, the highest level of staining was 5% in some airways (Halbert et al., supra (1998)). However, the overall efficiency of transduction in the airway epithelium was still low, approximately 2%. These transduction rates, nonetheless, represent a significant increase over those obtained previously with lower titer vector preparations (Halbert et al., supra (1998)), and show that the AAV vector preparations of the present invention made with MTrep, CMVcap, and E4orf6 plasmids were fully active in vivo.

Production of AAV6 pseudotyped recombinant AAV vectors was achieved by calcium phosphate transfection of 293 cells with the AAV2 vector ARAP4, the CMVE4orf6 plasmid and either MTrep and CMVcap6 plasmids or MTrep6 and CMVcap6 plasmids. AAV6 pseudotyped recombinant vectors produced from cells transfected with AAV2 vector ARAP4, the CMVE4orf6 plasmid, MTrep and CMVcap6 plasmids are termed Rep2Cap6Vector2 vectors. The AAV6 pseudotyped recombinant vectors produced from cells transfected with AAV2 vector ARAP4, the CMVE4orf6 plasmid, MTrep6 and CMVcap6 plasmids are termed Rep6Cap6Vector2 vectors. The AAV6 pseudotyped recombinant vectors produced from cells transfected with AAV6 vector ARAP4, the CMVE4orf6 plasmid, MTrep6 and CMVcap6 plasmid are termed Rep6Cap6Vector6 vectors. The AAV6-pseudotyped vectors were generated essentially as described above. Mice were given between $1-7\times10^{11}$ genome-containing particles by nasal aspiration and one month later their lungs were analyzed for AP expression as described (Halbert et al., supra).

Figure 4:
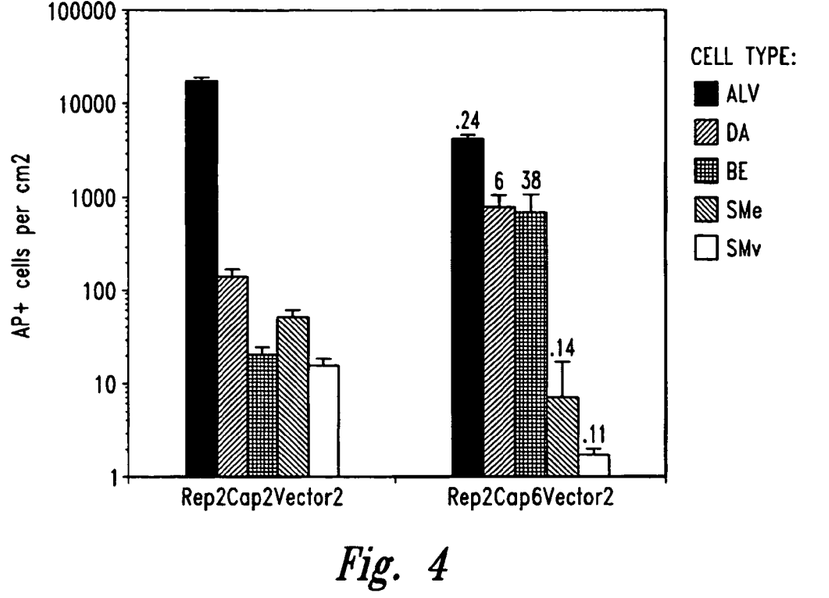
FIG. 4 depicts a histological analysis of lung sections from animals which received nasal aspirates of the Rep2Cap2Vector2 vector and Rep2Cap6Vector2 vector carried out one-month post aspiration. The animals were euthanized and the number of AP$^+$ alveolar cells (Alv—black rectangles), distal airway epithelial cells (DA—dark hatched rectangles), bronchial airway epithelial cells (BE—gray rectangles), smooth muscle cells underlying the epithelium (SMe—light hatched rectangles) and vascular smooth muscle cells (SMv—white rectangles) were quantified. The histograms show the number of AP+ cells for each vector pseudotype per cm² for each cell type.
Figure 5:
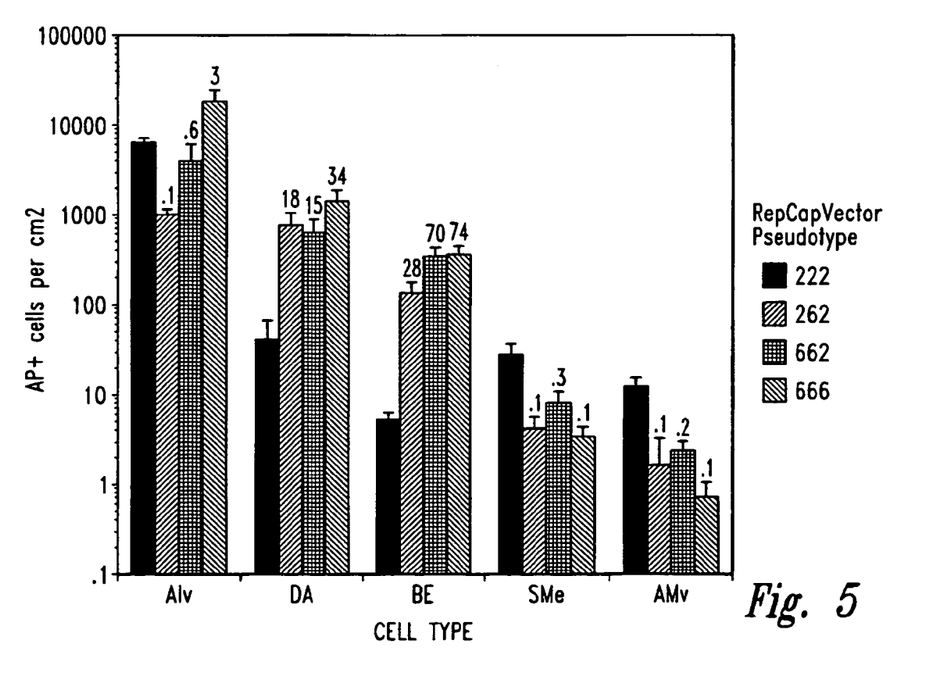
FIG. 5 depicts a histological analysis of lung sections from animals which received nasal aspirates of the AAV vectors carried out one-month post aspiration. The animals were euthanized and the number of AP+ alveolar cells (Alv), distal airway epithelial cells (DA), bronchial airway epithelial cells (BE), smooth muscle cells underlying the epithelium (SMe) and vascular smooth muscle cells (AMv) were quantified. The histograms show the number of AP+ cells for each vector pseudotype per cm² for each cell type. RepCapVector pseudotypes are Rep2Cap2Vector2 vector (222—black rectangles), Rep2Cap6Vector2 vector (262—dark hatched rectangles), Rep6Cap6Vector2 vector (662—gray rectangles) and Rep6Cap6Vector6 vector (666—light hatched rectangles).

The lungs exhibited dramatic AP staining of airway epithelium relative to AAV2 transfected control animals (FIGS. 4 and 5). As shown in FIG. 4, in a comparison between $AP^+$ cells per $cm^2$ from the lungs of AAV2 (Rep2Cap2Vector2) control vector-treated mice and $AP^+$ cells per $cm^2$ from the lungs of Rep2Cap6Vector2 vector-treated mice, there was a marked increase in the $AP^+$ cells in the distal airway epithelium and bronchial epithelium in Rep2Cap6Vector2 vector-treated mice. In a comparison of lung cell types in AAV2 vector-, Rep2Cap6Vector2 vector-, Rep6Cap6Vector2 vector-, and AAV6 vector-treated mice, the Rep2Cap6Vector2 vector- and Rep6Cap6Vector2 vector-treated mice exhibited elevated transduction ($AP^+$ cells per $cm^2$) in distal airway epithelium and bronchial epithelium and reduced transduction into alveolar epithelial cells. This demonstrates that AAV6 cap pseudotype vectors exhibit a dramatic increase in transduction of airway epithelium compared to AAV2 cap pseudotype vectors (FIG. 5).

Discussion:

The present invention provides methods for the production of AAV vector which requires a reduced number of adenovirus proteins to "help" when human 293 cell were transduced with a single adenovirus protein designated E4orf6 protein. While physical techniques such as cesium chloride density centrifugation or affinity chromatography followed by heat inactivation can eliminate infectious adenovirus from vector stocks, the potential for adenovirus protein contamination remains (Zolotukkin et al., Gene Ther. 6:973–985 (1999)). The present invention provides AAV vector production with the fewest number of potentially immunogenic contaminating adenovirus proteins and is thus advantageous for the preparation of clinical grade reagents.

AAV vector transduction of airway epithelia, a target tissue for the treatment of cystic fibrosis, is very low relative to other target organs, such as, liver or muscle. Cultured airway epithelial cells are also transduced at much lower rates by AAV vectors than are immortalized cell lines such as HeLa or 293 cells (Halbert et al, J. Virol. 69:1473–1479 (1995); Teramoto et al., J. Virol. 72:8904–8912 (1998), each incorporated herein by reference). In addition, treatments that have enhanced AAV transduction such as adenovirus co-infection or genotoxic agents are also less effective on airway epithelium (Teramoto et al., supra, (1998)). However, by the presently described methods it was possible to transduce up to 20% of lung airway epithelium in vivo with a recombinant AAV comprising a helper-free ARAP4 vector stock. The high level of transduction observed in vivo can be attributed to the ability to generate significantly higher titer vector stocks relative to that obtained by other methods. Indeed, the substitution of the separate MTrep and CMVcap plasmids for MTrep/CMVcap, and CMVE4orf6 for adenovirus infection increased productivity by about 20-fold.

It must be noted that many strategies, including the use of stable packaging lines, have been described to generate large quantities of AAV vectors (Clark et al., Hum. Gene Ther. 6:1329–1341 (1995); Flotte et al., Proc. Natl. Acad. Sci. USA 90:10613–10617 (1995); Allen et al., J. Virol. 71:6816–6822 (1997); Li et al., J. Virol. 71:5236–5243 (1997); Vincent et al., (1997), Gao et al., Hum. Gene Ther. 9:2353–2362 (1998); Grimm et al., Hum. Gene Ther. 9:2745–2760(1998); Inoue and Russell, J. Virol. 72:7024–7031 (1998); Matsushita et al., Gene Ther. 5:938–945 (1998); Xiao et al., J. Virol. 72:2224–2232 (1998); Clark et al., Hum. Gene Ther. 10:1031–1039 (1999), each incorporated herein by reference). A comparison of the vector yields from these strategies is difficult due to differences in vector transduction assays which have been used in the art to characterize the packaging lines. For example, it has been common practice by many to titer AAV vector stocks on target cells in the presence of adenovirus co-infection. Adenovirus co-infection with AAV vectors has been shown to facilitate the conversion of the incoming single-stranded AAV vector genomes to "transcriptionally-active" double stranded forms (Ferrari et al., J. Virol. 70:3227–3234 1996); Fisher et al., Nature Med. 3:306–312 (1996), incorporated herein by reference). It is unclear whether the "increase" represents the transduction potential of the vector stock and only reduces the time required for the assay or is an overestimate of the titer. When similar vector stocks have been assayed in the presence or absence of adenovirus co-infection, the increase can approach 1000-fold in some cell types while it is only two to seven-fold in others (Teramoto et al., J. Virol. 72:8904–8912 (1998)).

The present results provide additional evidence that vector titer assayed in the absence of adenovirus co-infection more closely models transduction for clinical applications. In addition, adenovirus infection of target cells results in cytopathic effects and eventual cell death precluding studies to examine long-term expression of transgenes. Table 1 provides a comparison of data disclosed herein with results previously reported for AAV vector production using various transient transfection packaging systems derived from the initial AAV/Ad packaging plasmid. A "corrected" adenovirus-free titer has been calculated to reflect the increase in transduction due to the co-infection of target cells with adenovirus plus AAV vector stocks. The correction factors for 293 cells and HeLa target cells (40 and 300, respectively) were derived from Teramoto et al., J. Virol. 72:8904–8912 (1998), incorporated herein by reference). The authors refer to values as high as 1000-fold for these target cells in the text, but the more conservative values above were selected from the data presented. The value determined for the AAV vector yield using ACG-2 plus adenovirus is within 5-fold of the corrected literature values (1.2 versus 5.5 TU per cell; Table 1). Helper-free AAV vector production with MTrep+CMVcAP+E4orf6 was approximately 20-fold higher than the yield demonstrated herein with the ACG-2 plus adenovirus and at least 6-fold higher than the corrected helper-free ACG-2 yield reported in the literature (Table 1).

AAV vector genome analysis is also a commonly used method to quantify production yields independent of the nature of the vector sequences. This method is very sensitive but requires the removal of all contaminating plasmid and replicative form DNA, especially when assayed by slot hybridization or polymerase chain reaction assays. Southern blot analysis of DNase treated vector virions can distinguish between packaged single stranded genomes and incompletely digested plasmid and/or replicative form DNA. In the present study genome containing particle yields of approximately $10^4$ per cell transfected and vector genome to infectivity ratios of approximately $10^2$ were observed, a ratio consistent with values presented in the literature (Salvetti et al., *Hum. Gene Ther.* 9:695–706 (1998); Matsushita et al., *Gene Ther.* 5:938–945 (1998); Xiao et al., *J. Virol.* 72:2224–2232 (1998); Gao et al., *Hum. Gene Ther.* 9:2353–2362 (1998); Grimm et al., Hum. Gene Ther.

and the achievement of significantly higher yields using the separate rep and cap plasmids provided improved vector stocks for preclinical and clinical applications. The increase in AAV vector production allowed for the administration of significantly larger amounts of the ARAP4 vector in a murine lung model resulting in the highest level of transduction in airway epithelium yet observed and reported.

AAV rep and AAV cap genes from adeno-associated virus type 6 have also been used to construct packaging cells of the present invention. The packaging cells comprising AAV 6 rep and AAV 6 cap also produced recombinant AAV vector at high efficiency. Further, evidence is provided that AAV6 cap pseudotype vectors show preferential transduction into distal airway epithelium and bronchial epithelium relative to AAV2 cap pseudotype vectors.

TABLE 1

AAV vector yields using different production strategies.

| Vector Production Procedure | | | | | | |
|---|---|---|---|---|---|---|
| AAV | Adenovirus | | Vector Assay | | | |
| Packaging Plasmid | helper components | Target cells for vector assay | Reported[1] TU per cell | Adenovirus[2] correction factor | Adenovirus-free[3] TU per cell | References |
| AAV/Ad | + Ad | 293 | 28 | 40 | 0.7 | Li[6] |
| ACG-2 | + Ad | 293 | 220 | 40 | 5.5 | Li[6] |
| PXX2 | E4/E2A/VA | HeLa | 1100 | 300 | 3.7 | Xiao[7] |
| ACG-2 | E4/E2/VA | C12 (HeLa) | 1 | 300[4] | 0.003 | Zolotukhin[8] |
| PDG | E4/E2/VA | C12 (HeLa) | 209 | 300[4] | 0.7 | Zolotukhin[8] |
| ACG-2 | + Ad | IB3 | NA[5] | NA | 1.2 | |
| MTrep/CMVcap | + Ad | IB3 | NA | NA | 1.6 | |
| MTrep/CMVcap | E4orf6 | IB3 | NA | NA | 1.0 | |
| MTrep + CMVcap | + Ad | IB3 | NA | NA | 7.0 | |
| MTrep + CMVcap | E4orf6 | IB3 | NA | NA | 23 | |

[1]AAV vector yield (TU-transduction Units) as reported after co-infection of target cells with adenovirus.
[2]Adenovirus correction factor determined from ratio of AAV vector titer measured with adenovirus co-infection divided by that obtained without adenovirus on indicated target cells as described (Teramoto et al., J. Virol. 8904-8912 (1998)).
[3]Reported TU per cell in the presence of adenovirus divided by the adenovirus correction factor.
[4]The adenovirus correction factor for C12 cells is assumed to be the same as the parental HeLa cells. C12 cells are a HeLa-based line expressing the rep and cap genes (Clark et al., Hum. Gene Ther. 10:1031–1039 (1999)). The impact of expressing the AAV rep and cap genes in the target cells is unknown, but might be expected to further increase the apparent AAV vector titer.
[5]Not Applicable
[6]Li et al., J. Virol. 71:5236–5243 (1997)
[7]Xiao et al., J. Virol. 72:2224–2232 (1998)
[8]Zolotukhin et al., Gene Ther. 6:973–985 (1999)

9:2745–2760 (1998); Mah et al., *J. Virol.* 72:9835–9843 (1998); Qing et al., (1998); Summerford et al., *Nature Med.* 5:78–82 (1998); Qing et al., *Nature Med.* 5:71–77 (1999); Summerford et al., (1999); Clark et al., *Hum. Gene Ther.* 10:1031–1039 (1999), each incorporated herein by reference). The ambiguity introduced by differences in the methodologies used in determining the titer of AAV vector preparations prompted the inclusion of ACG-2 plasmid as an internal control for vector production using the MTrep/CMVcap packaging plasmid in the present study. The data provided herein are consistent with the calculated values presented in Table 1.

The finding that only a single adenovirus helper protein, E4orf6, was required to produce AAV vectors in 293 cells While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated herein by reference in their entirety for all purposes to the same extent as if each individual publication or patent document were so individually denoted.

What is claimed is:

1. A mammalian cell which can package a recombinant adeno-associated virus (AAV) vector at high efficiency, the cell comprising a polynucleotide sequence comprising an AAV cap gene operably linked to a heterologous promoter, a polynucleotide sequence comprising an AAV rep gene operably linked to a promoter, and a polynucleotide sequence consisting of an adenovirus E4orf6 gene as the single adenovirus gene to provide helper virus functions.

2. The mammalian cell of claim 1, wherein the promoter operably linked to the AAV rep gene is a second heterologous promoter.

3. The mammalian cell of claim 2, wherein the heterologous promoter operably linked to the AAV rep gene and operably linked to the AAV cap gene are the same promoter.

4. The mammalian cell of claim 2, wherein the heterologous promoter operably linked to the AAV rep gene and operably linked to the AAV cap gene are different promoters.

5. The mammalian cell of claim 2, wherein the heterologous promoter is inducible.

6. The mammalian cell of claim 1, wherein the heterologous promoter operably linked to the AAV cap gene is a cytomegalovirus promoter.

7. The mammalian cell of claim 6, wherein the cytomegalovirus promoter is the cytomegalovirus major IE gene promoter.

8. The mammalian cell of claim 5, wherein the heterologous promoter operably linked with the AAV rep gene is a metallothionein promoter.

9. The mammalian cell of claim 8, wherein the heterologous promoter is a murine metallothionein I (MT-1) promoter.

10. The mammalian cell of claim 1, further comprising a recombinant AAV (rAAV) vector, wherein the vector comprises a polynucleotide sequence of interest positioned between two AAV terminal repeat regions, wherein the mammalian cell is a cultured cell.

11. The mammalian cell of claim 1, wherein the AAV rep and the AAV cap genes are provided as AAV split-packaging genes.

12. The mammalian cell of claim 11, wherein the promoter operably linked to the AAV rep gene is a second heterologous promoter.

13. The mammalian cell of claim 12, wherein the heterologous promoter operably linked to the AAV rep gene and the heterologous promoter operably linked to the AAV cap gene are the same.

14. The mammalian cell of claim 12, wherein the heterologous promoter operably linked to the AAV rep gene and operably linked to the AAV cap gene are different.

15. The mammalian cell of claim 11, wherein the polynucleotide sequences which comprise the AAV rep and AAV cap genes are provided on separate vectors.

16. The mammalian cell of claim 11, wherein the polynucleotide sequences which comprise the AAV rep and AAV cap genes are provided on the same vector separated by non-AAV oligonucleotide sequence.

17. The mammalian cell of claim 1, wherein the adenovirus E4orf6 gene is operably linked to a heterologous promoter.

18. The mammalian cell of claim 17, wherein the heterologous promoter is inducible.

19. The mammalian cell of claim 17, wherein the heterologous promoter is a cytomegalovirus promoter.

20. The mammalian cell of claim 1, wherein the AAV rep gene and the AAV cap gene are the AAV type 2 rep gene and the AAV type 2 cap gene.

21. The mammalian cell of claim 1, wherein the AAV rep gene and the AAV cap gene are the AAV type 6 rep gene and the AAV type 6 cap gene.

22. The mammalian cell of claim 1, wherein the AAV rep gene and the AAV cap gene are AAV rep and cap genes of different AAV types.

23. The mammalian cell of claim 22, wherein the AAV rep gene is the AAV 6 rep gene and the AAV cap gene is the AAV 2 cap gene.

24. The mammalian cell of claim 22, wherein the AAV rep gene is the AAV 2 rep gene and the AAV cap gene is the AAV 6 cap gene.

25. The mammalian cell of claim 17, wherein the adenovirus E4orf6 gene is a adenovirus type 5 E4orf6 gene.

26. A method for the production of recombinant AAV vector, comprising the steps of:
   a) providing a mammalian cell which can package a recombinant AAV vector at high efficiency, the cell comprising a polynucleotide sequence comprising an AAV cap gene operably linked to a heterologous promoter, a polynucleotide sequence comprising an AAV rep gene operably linked to a promoter, and a polynucleotide sequence consisting of an adenovirus E4orf6 gene as the single adenovirus gene to provide helper virus functions;
   b) introducing a recombinant vector comprising a polynucleotide of interest positioned between two AAV terminal repeat (TR) regions; and
   c) incubating the cell under conditions conducive to replication and packaging of the recombinant AAV vector.

27. The method of claim 26, wherein the AAV rep and the AAV cap genes are provided as an AAV split-packaging gene.

28. The method of claim 27, wherein the AAV rep and the AAV cap genes are provided as separate vector constructs.

29. The method of claim 26, wherein the mammalian cell is a human cell transfected with a first vector comprising a polynucleotide sequence comprising the AAV rep gene operably linked to a murine metallothionein I promoter; a second vector comprising a polynucleotide sequence comprising the AAV cap gene operably linked to a cytomegalovirus promoter; a third vector comprising a polynucleotide sequence consisting of the E4orf6 gene as the single adenovirus gene to provide helper virus functions; and a fourth vector comprising a polynucleotide of interest positioned between two AAV terminal repeat (TR) regions.

30. A method for the production of a mammalian cell which can package a recombinant AAV vector at high efficiency, comprising:
   transducing a mammalian host cell susceptible to infection by AAV with a first vector comprising a polynucleotide sequence comprising an AAV cap gene operably linked to a heterologous promoter;
   transducing the mammalian cell with a second vector comprising a polynucleotide sequence comprising an AAV rep gene operably linked to linked to a promoter;
   transducing the mammalian cell with a third vector comprising a polynucleotide sequence consisting of an adenovirus E4orf6 gene as the single adenovirus gene to provide helper virus functions; and
   growing the transduced host cell under conditions conducive for the replication and selection of transduced mammalian cells comprising the polynucleotide sequences comprising the AAV rep gene, the AAV cap gene, and the polynucleotide sequence comprising the adenovirus E4orf6 gene.

31. The method of claim 30, wherein the E4orf6 gene is an adenovirus type 5 E4orf6 gene.

32. The method of claim 30, wherein the AAV cap gene is the AAV 2 cap gene.

33. The method of claim 32, wherein the AAV rep gene is the AAV 2 rep gene.

34. The method of claim 30, wherein the AAV cap gene is the AAV 6 cap gene.

35. The method of claim 34, wherein the AAV rep gene is the AAV 6 rep gene.

36. The method of claim 30, wherein the AAV cap gene and the AAV rep gene are of different AAV types.

* * * * *